(12) United States Patent
Aune (10) Patent No.: US 10,234,373 B2
(45) Date of Patent: Mar. 19, 2019

(54) RESISTIVE TYPE PARTICLE DETECTION DEVICE AND PARTICLE DETECTION METHOD

(71) Applicant: COMMISSARIAT A L'ENERGIE ATOMIQUE ET AUX ENERGIES ALTERNATIVES, Paris (FR)

(72) Inventor: Stephan Aune, Palaiseau (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 134 days.

(21) Appl. No.: 15/190,573

(22) Filed: Jun. 23, 2016

(65) Prior Publication Data

US 2016/0377522 A1 Dec. 29, 2016

(30) Foreign Application Priority Data

Jun. 23, 2015 (FR) ...................................... 15 55754

(51) Int. Cl.
*G01N 15/10* (2006.01)
*G01T 1/29* (2006.01)
*H01J 47/02* (2006.01)
*G01T 1/185* (2006.01)

(52) U.S. Cl.
CPC ......... *G01N 15/1031* (2013.01); *G01T 1/185* (2013.01); *G01T 1/2935* (2013.01); *H01J 47/02* (2013.01)

(58) Field of Classification Search
CPC ... G01N 15/1031; G01T 1/185; G01T 1/2935; H01J 47/02

USPC ................................................ 324/693, 71.4
See application file for complete search history.

(56) References Cited

U.S. PATENT DOCUMENTS

| 6,011,265 A * | 1/2000 | Sauli ....................... H01J 47/02 250/374 |
| 2011/0272591 A1* | 11/2011 | De Oliveira ............ G01T 1/185 250/385.1 |
| 2015/0041665 A1* | 2/2015 | Hollebeek ............. A61N 5/1071 250/375 |

OTHER PUBLICATIONS

Search Report as issued in French Patent Application No. 1555754, dated Apr. 26, 2016.
Bortfeldt, J., "Development of Floating Strip Micromegas Detectors," 2014, Retrieved from the Internet, <https://edoc.ub.uni-muenchen.de/16972/1/Borfeldt_Jonathan.pdf>. Retrieved on Apr. 15, 2016, pp. 27-34.
Iakovidis, G., "The Micromegas project for the ATLAS upgrade," Journal of Instrumentation, Institute of Physics Publishing, vol. 8, No. 12, Dec. 9, 2013, ISSN: 1748-0221, 10 pages.

(Continued)

*Primary Examiner* — Jeff W Natalini
(74) *Attorney, Agent, or Firm* — Pillsbury Winthrop Shaw Pittman LLP (57) ABSTRACT

A resistive type particle detection device includes a cathode, an amplification micro-gate, and an anode composed of a flat insulator including resistive tracks arranged on a face of the flat insulator facing the amplification micro-gate and reading tracks arranged on the opposite face of the flat insulator, the reading tracks being connected to a reading system. In a non-limiting embodiment, the resistive type particle detection device further includes a conductive track positioned between two resistive tracks.

9 Claims, 4 Drawing Sheets

(56) References Cited

OTHER PUBLICATIONS

Procureur, S., et al., "Operation of a resistive Micromegas in air," Nuclear Instruments and Methods in Physics Research, Section A: Accelerators, Spectrometers, Detectors, and Associated Equipment, Elsevier BV, vol. 688, Jun. 11, 2012, pp. 75-79.

Jeanneau, F., et al., "Performances and ageing study of resistive-anodes Micromegas detectors for HL-LHC environment," Nuclear Science Symposium and Medical Imaging Conference (NSS/MIC), 2011 IEEE, Oct. 23, 2011, ISSN: 978-1-4673-0118-3, pp. 75-79.

Byszewski, M., et al., "Resistive-strips micromegas detectors with two-dimensional readout," Journal of Instrumentation, Institute of Physics Publishing, vol. 7, No. 2, Feb. 28, 2012, ISSN: 1748-0221, 8 pages.

\* cited by examiner

RESISTIVE TYPE PARTICLE DETECTION DEVICE AND PARTICLE DETECTION METHOD

CROSS-REFERENCE TO RELATED APPLICATIONS

This application claims priority to French Patent Application No. 1555754, filed Jun. 23, 2015, the entire content of which is incorporated herein by reference in its entirety.

FIELD

The present invention relates to a resistive type particle detection device, such as a detector of gaseous particles known as "micromegas detector" (for "MICRO MEsh GAseous Structure"). The invention also relates to a particle detection method implementing a resistive type particle detection device in accordance with that of the invention.

BACKGROUND

Micromegas detectors are known comprising a gas enclosure that is filled with a suitable gaseous mixture, such a detector enabling the amplification of electrons by an avalanche process.

Figure 1:
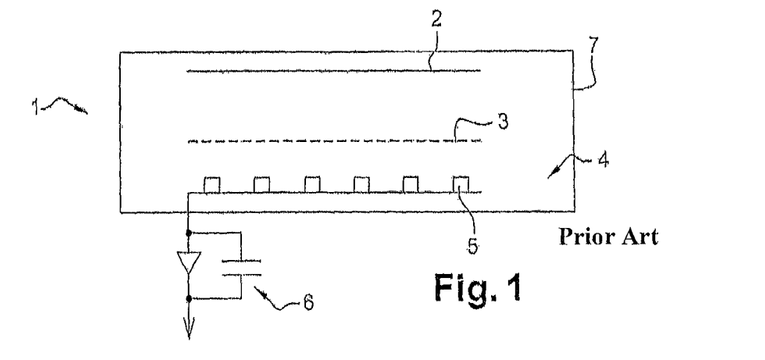
FIG. 1 represents, schematically, an example of embodiment of a particle detection device according to the prior art.

As illustrated in FIG. 1, a first category of micromegas detector 1 relates to conventional micromegas detectors comprising notably a cathode 2, an amplification micro-gate 3 and an anode 4 provided with reading tracks 5 connected to a reading device 6. The cathode 2, the amplification micro-gate 3 and the anode are arranged in a gas enclosure 7. The cathode 2 diverts the electrons to the reading tracks 5, whereas the amplification micro-gate 3 makes it possible to amplify the signal so that it is read. In order to amplify the signal passing through the amplification micro-gate 3, an electric voltage of approximately 500 V is applied to the amplification micro-gate 3.

During the implementation of such a micromegas detector 1, the electric voltage is increased progressively on the amplification micro-gate 3 until 500 V are obtained. Above this value of 500 V, sparks appear between the amplification micro-gate 3 and the reading tracks 5 making the micromegas detector 1 momentarily inoperative. Normally, the sparks develop where impurities are situated, in other words between the reading tracks 5 and the amplification micro-gate 3. Then, the plasma of the spark vaporises the impurity and the voltage may continue to be increased up to the value of 500 V.

Moreover, sparks may also be produced when the micromegas detector 1 is operational. These sparks generally appear when the flux of particles becomes too intense. The micromegas detector 1 then undergoes breakdowns making the voltage drop and discharging the amplification micro-gate 3. During the time taken to re-establish the electric voltage of the amplification micro-gate 3, around 1 ms, the micromegas detector 1 is inoperative.

The development of breakdowns in the micromegas detector 1 is often a limiting factor in extreme conditions of use, notably in very high particle fluxes generating therein drops in gain as well as a possible degradation of the micromegas detector 1 in the long term.

Figure 2:
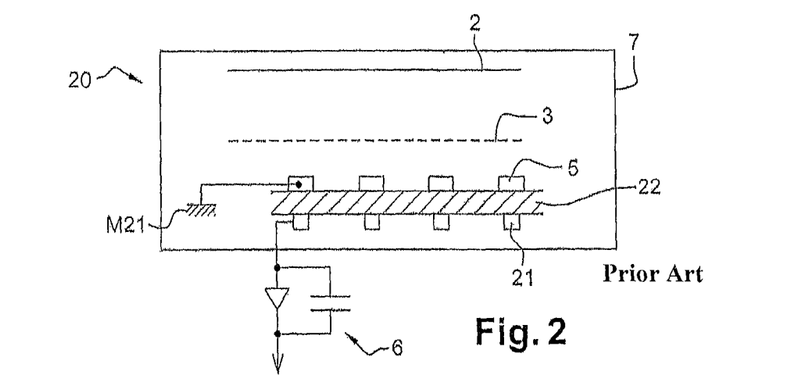
FIG. 2 represents, schematically, a different example of embodiment of a particle detection device according to the prior art.

In order to reduce the amplitude and the impact of breakdowns, a second category of micromegas detector 20 has been developed, namely so-called resistive micromegas detectors. As illustrated in FIG. 2, this type of resistive micromegas detector 20, moreover comprises resistive tracks 21 connected to the common ground M21 and positioned facing reading tracks 5. The reading tracks 5 and the resistive tracks 21 are moreover separated by an insulating layer 22. The presence of these resistive tracks 21 makes it possible to avoid the formation of the breakdown, and to evacuate the charges to the common ground M21. Hence, resistive micromegas detectors 20 are particularly sensitive to impurities. In fact, not being able to break down, it is no longer possible to eliminate the impurities during the powering up of the amplification micro-gate 3. If an impurity is present or is introduced into the resistive micromegas detector 20, an important leakage current makes the whole of the resistive micromegas detector 20 difficult to use. Also, resistive micromegas detectors 20 have to be assembled in a clean room so as to reduce the risk of introducing dust. The use of a clean room for the assembly of resistive micromegas detectors 20 in order to leave the minimum of dust on the reading tracks 5 significantly increases the manufacturing costs without however guaranteeing 100% cleanliness reliability.

Moreover, despite assembly in a clean room, resistive micromegas detectors remain not very reliable for usage outside of the laboratory. In fact, it is possible that a dust of around 50 μm is introduced via the introduction of gas into the gas enclosure. To overcome this problem, numerous pressurised water washings are regularly carried out.

SUMMARY

An aspect of the invention aims to resolve the aforementioned problems of the prior art. More particularly, a problem that an aspect of the invention proposes resolving is to provide a micromegas detector of which the manufacturing conditions are reasonable, while assuring optimum operating reliability.

To this end, an aspect of the invention pertains to a resistive type particle detection device including:
 a cathode,
 an amplification micro-gate, and
 an anode composed of a flat insulator comprising resistive tracks arranged on a face of the flat insulator facing the amplification micro-gate and reading tracks arranged on the opposite face of the flat insulator, the reading tracks being connected to a reading system.

Moreover, the resistive type particle detection device comprises at least one conductive track positioned between two resistive tracks.

Thanks to the conductive track positioned between two resistive tracks, the particle detection device is self-cleaning. At start-up but also during its life, if dusts are generated and/or introduced, the conductive track is connected up to the ground in order to generate electric fields and to induce a spark which eliminates the impurities.

Since the impurities may be implemented during the start-up of the device, it is not necessary to assembly the device in a clean room and the manufacturing cost is thereby reduced. Moreover, since the impurities may be eliminated in operation, the reliability of the particle detection device is improved.

Apart from the main characteristics that have been mentioned in the preceding paragraph, the resistive type particle detection device according to the invention may have one or more of the additional characteristics below, considered individually or according to any technically possible combinations thereof.

In a non-limiting embodiment, the resistive type particle detection device comprises at least one conductive track out of ten resistive tracks.

In a non-limiting embodiment, the resistive type particle detection device comprises an alternation of conductive tracks and resistive tracks.

In a non-limiting embodiment, the maximum distance separating a conductive track from a neighbouring resistive track is equal to half of the step separating two resistive tracks situated on either side of the conductive track less half of the width of said conductive track.

In a non-limiting embodiment, the electric connections of the resistive tracks and/or conductive tracks are situated outside of a sealed enclosure comprising the cathode, the amplification micro-gate, and the anode.

In a non-limiting embodiment, the resistive tracks and the conductive track are physically independent of each other.

In a non-limiting embodiment, the resistive type particle detection device comprises at least one electric contact, the electric contact being connected at a first end to a first resistive track and at a second end to a second resistive track, the conductive track positioned between the two resistive tracks being sectioned at the level of the at least one electric contact, two sections of the conductive track being connected together via a connection track arranged in the flat insulator.

Another aspect of the invention pertains to a method for detecting particles implementing a resistive type particle detection device according to the invention.

In a non-limiting embodiment, the method for detecting particles comprises, in particle detection mode, the following steps:
  Application of a first determined electric voltage to the cathode,
  Application of a second determined electric voltage to the amplification micro-gate,
  Establishment of an electric connection between the reading tracks and the reading system,
  Establishment of an electric connection between the resistive tracks and a ground, and
  Establishment of a floating connection to the conductive track.

In a non-limiting implementation, the method for detecting particles comprises, in impurities cleaning mode, the following steps:
  Application of a first determined electric voltage to the cathode,
  Application of a second determined electric voltage or a voltage ramp to the amplification micro-gate,
  Establishment of an electric connection between the reading tracks and the reading system or a floating connection of the reading tracks,
  Establishment of an electric connection between the resistive tracks and a ground, and
  Establishment of an electric connection between the conductive track and a ground.

In a non-limiting implementation, the method for detecting particles comprising, in amplification optimisation mode, the following steps:
  Application of a first determined electric voltage to the cathode,
  Application of a second determined electric voltage or a voltage ramp to the amplification micro-gate,
  Establishment of an electric connection between the reading tracks and the reading system,
  Establishment of an electric connection between the resistive tracks and a ground, and
  Application of a third determined electric voltage to the conductive track, the third determined electric voltage being negative.

DESCRIPTION OF THE FIGURES

Other characteristics and benefits of the invention will become clearer from the description that is given thereof hereafter, as an indication and in no way limiting, with reference to the appended figures among which.

For reasons of clarity, only elements useful for the understanding of the invention have been represented, and have been done so without respect for scale and in a schematic manner. Moreover, similar elements situated in the different figures bear identical references.

DETAILED DESCRIPTION

FIGS. 1 and 2 have already been described previously with reference to the prior art.

Figure 3:
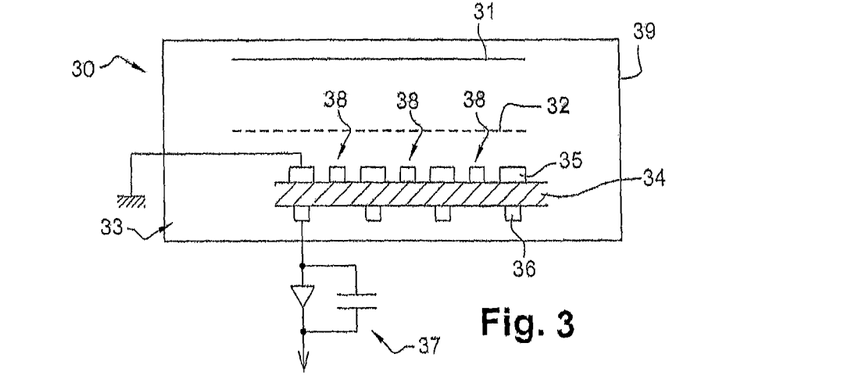
FIG. 3 represents, schematically, a first example of embodiment of a particle detection device according to an embodiment of the invention.

FIG. 3 illustrates a resistive type particle detection device 30 in accordance with that of the invention. The resistive type particle detection device 30 comprises:
  a cathode 31,
  an amplification micro-gate 32, and
  an anode 33, this anode 33 comprising a flat insulator 34 (forming a substrate) comprising resistive tracks 35 arranged on a face of the flat insulator 34 and facing the amplification micro-gate 32. The anode 33 also comprises reading tracks 36 arranged on the opposite face of the flat insulator 34, the reading tracks 36 being connected to a reading system 37.

Figure 4:
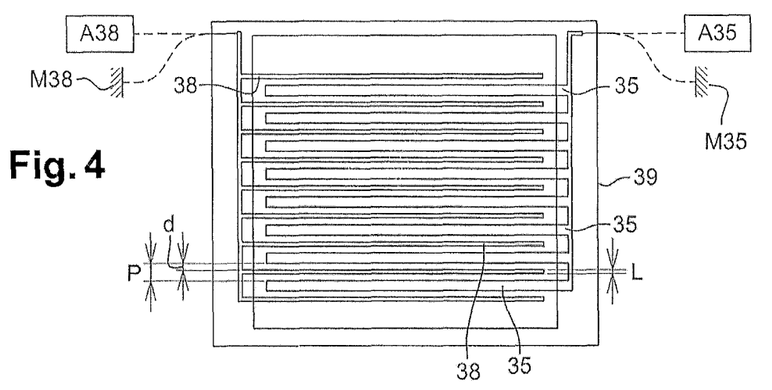
FIG. 4 illustrates a top view of the particle detection device illustrated in FIG. 3.

The resistive type particle detection device 30 further comprises, in the example illustrated, several conductive tracks 38, each conductive track 38 being positioned between two resistive tracks 35. This alternation of resistive tracks 35 and conductive tracks 38 on the active surface of the particle detection device 30 situated under the amplification micro-gate 32 is illustrated in FIG. 4.

It should be noted that the resistive tracks 35 may be connected to a same voltage supply of the resistive tracks A35 (or to the ground M35) and the conductive tracks 38 may also be connected to a same voltage supply of the conductive tracks A38 (or to the ground M38). In this non-limiting implementation, the electric connections made between the resistive tracks 35 and the voltage supply of the resistive tracks A35 (or to the ground M35) are formed outside of a sealed enclosure 39 comprising the cathode 31, the amplification micro-gate 32, and the anode 33. Similarly, the electric connections made between the conductive tracks 38 and the voltage supply of the conductive tracks A38 (or to the ground M38) are made outside of the sealed enclosure 39 comprising the cathode 31, the amplification micro-gate 32, and the anode 33. The fact that the electric connections are positioned outside of the gas tight frame formed by the sealed enclosure 39 makes it possible to electrically disconnect one or more resistive 35 and/or conductive 38 tracks without opening, and thus polluting, the resistive type particle detection device 30.

In order to avoid perturbing the operation of the particle detection device 30, it is beneficial that the two types of tracks, namely the resistive tracks 35 and the conductive tracks 38, do not have contact with each other. The conductive tracks 38 and the resistive tracks 35 are thus physically independent of each other (infinite Ohmic contact). In other words, the conductive tracks and the resistive tracks do not touch physically.

The conductive tracks 38 may be formed by screen printing of polymer paste filled with conductor, for example copper oxide.

In a non-limiting implementation, the conductive tracks 38 are made of copper on the flat insulator 34, which flat insulator 34 may be made of Kapton®.

In a non-limiting implementation, the resistive tracks 35 are formed by the screen printing application of carbon filled polymer paste. To avoid any contact between the conductive tracks 38 and the resistive tracks 35, the screen printing spares the conductive tracks 38. If the positioning precision of the printing screen is not sufficient to avoid contact between the conductive tracks 38 and the resistive tracks 35, then a protective mask, for example formed by a UV polymerisable film, is used. This protective mask in fact makes it possible to protect the tracks formed first, for example the conductive tracks 38, and to enable the deposition of the second, in this non-limiting example, the resistive tracks 35.

The example illustrated in FIGS. 3 and 4 is in no way limiting. It is understood that the resistive type particle detection device 30 according to the invention may comprise a different number of conductive tracks 38, for example only one conductive track 38 out of ten resistive tracks 35.

In a beneficial example illustrated in FIG. 4, the maximum distance d separating a conductive track 38 and a neighbouring resistive track 35 is equal to half of the step p separating two resistive tracks 35 situated on either side of the conductive track 38 less half of the width L of the conductive track 38 situated between the two resistive tracks 35. Thus, for a step p of 500 µm between two resistive tracks 35 and a conductive track 38 having a width L of 80 µm, the maximum distance d between the conductive track 38 and the neighbouring resistive track 35 is d: (500/2)-(80/2)=210 µm. It follows that in this implementation the maximum distance between an impurity and a conductive track 38 will not exceed 210 µm. This distance is sufficiently low so that the electric field generated by the conductive track 38 can vaporise the dust.

Figure 5:
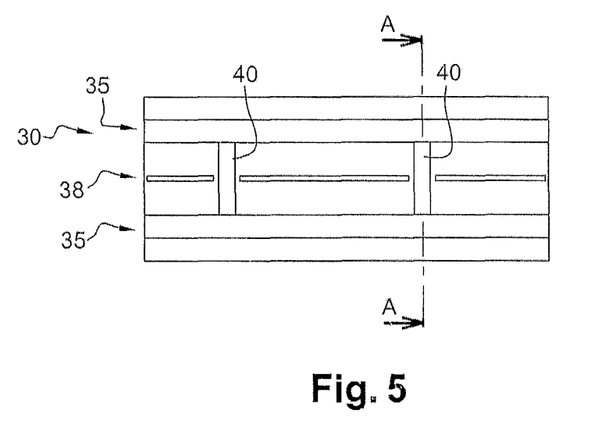
FIG. 5 illustrates, schematically, a second example of embodiment of a particle detection device according to the invention.
Figure 6:
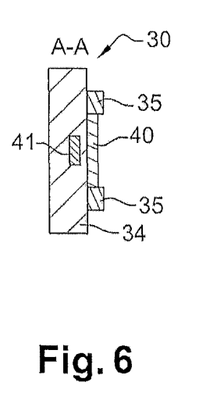
FIG. 6 represents, schematically, a sectional view A-A of the particle detection device represented in FIG. 5.

In a non-limiting example illustrated in FIG. 5, the particle detection device 30 comprises electric contacts 40 (also known as ladders). Each of the electric contacts 40 is connected at a first end to a first resistive track 35 and at a second end to a second resistive track 35. In this embodiment, the conductive track 38 (only one is represented for reasons of clarity) positioned between a first resistive track 35 and a second resistive track 35 is sectioned at the level of the electric contacts 40 connecting the first resistive track 35 and the second resistive track 35 in order not to touch the electric contacts 40. In this case, the conductive tracks 38 are constituted of segments connected together by the use of internal connection tracks positioned in the flat insulator. FIG. 6 is a view along the section A-A of FIG. 5 and represents a connection track 41 arranged in the flat insulator 34.

Generally speaking, the electric contacts 40 make it possible to increase the flow of charges and to avoid the electric voltage charging of the resistive tracks 35.

An aspect of the invention also relates to a method for detecting particles implementing a resistive type particle detection device 30 according to the invention.

Figure 7:
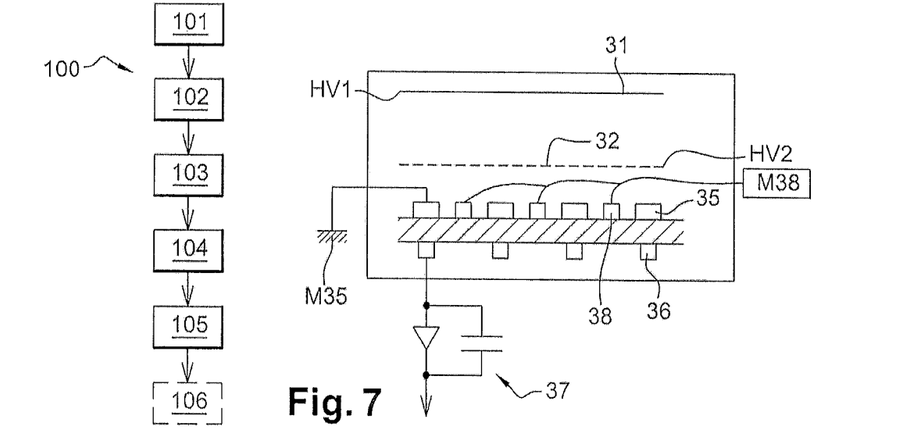
FIG. 7 illustrates a synoptic of the steps of a first mode of implementation of a method for detecting particles in accordance with an embodiment of the invention.

FIG. 7 represents a method 100 for detecting particles operating in particle detection mode and implementing a resistive type particle detection device 30 according to an embodiment of the invention.

In this non-limiting implementation, the method 100 for detecting particles comprises a step 101 of application of a first determined electric voltage HV1 to the cathode 31.

It also comprises a step 102 of application of a second determined electric voltage HV2 to the amplification micro-gate 32.

The method 100 further comprises a step 103 of establishing an electric connection between the reading tracks 36 and the reading system 37.

In addition, the method 100 implements a step 104 of establishing an electric connection between the resistive tracks 35 and a ground M35.

In this particle detection mode, the method 100 further comprises a step 105 of establishing a floating connection to the conductive track 38, in other words no electric voltage is applied and no connection to the ground M38 is established.

In such an implementation, the electric field present between the amplification micro-gate 32 and the resistive tracks 35 connected to the ground M35 directs the charges of the electron avalanche linked to the detection to the resistive tracks 35. If the conductive tracks 38 charge over time under the effect of collection of electrons due to the electron avalanche, and do so despite the absence of electric voltage, then the collection of electrons will be reduced because the charging will be negative. A reduction in the efficiency of the detector ensues therefrom.

If this reduction becomes bothersome, then the method 100 implements a step 106 (represented in dotted line in FIG. 7) of establishing a connexion to the ground M38 of the conductive tracks 38. Furthermore such a step may also be programmed and thus become systematic at predetermined time intervals.

Figure 8:
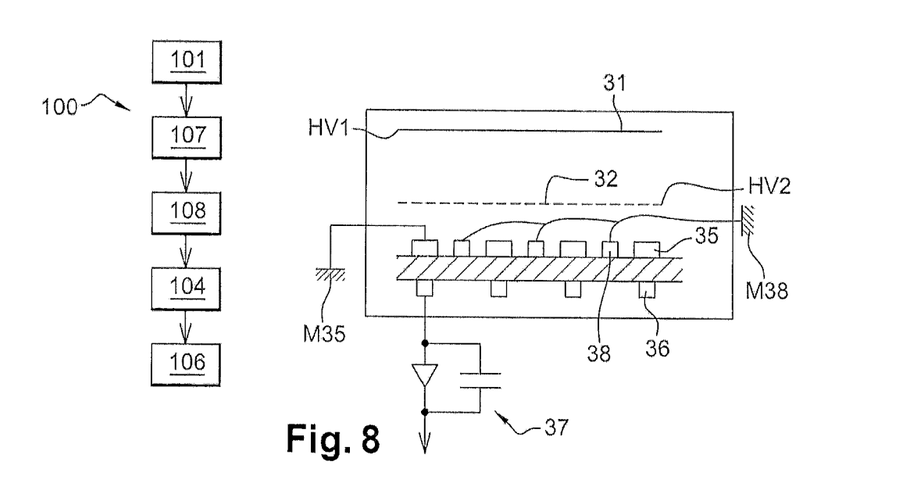
FIG. 8 illustrates a synoptic of the steps of a second mode of implementation of a method for detecting particles in accordance with an embodiment of the invention.

FIG. 8 represents a method 100 for detecting particles operating in impurities cleaning mode and implementing a resistive type particle detection device 30 according to an embodiment of the invention.

In this non-limiting implementation, the method 100 for detecting particles comprises a step 101 of application of a first determined electric voltage HV1 to the cathode 31.

It also comprises a step 107 of application of a second determined electric voltage HV2 or a voltage ramp (not illustrated) to the amplification micro-gate 32.

The method further comprises a step 108 of establishing an electric connection between the reading tracks 36 and the reading system 37 or a floating connection (illustrated in dotted line in FIG. 8) of the reading tracks 36.

It also comprises a step 104 of establishing an electric connection between the resistive tracks 35 and the ground M35.

In addition, the method 100 comprises a step 106 of establishing an electric connection between the conductive track 38 and the ground M38.

In such an implementation, this layout makes it possible to generate electric fields in the enclosure 39 and to induce a spark at the places where the impurities are located and thus to eliminate them.

Figure 9:
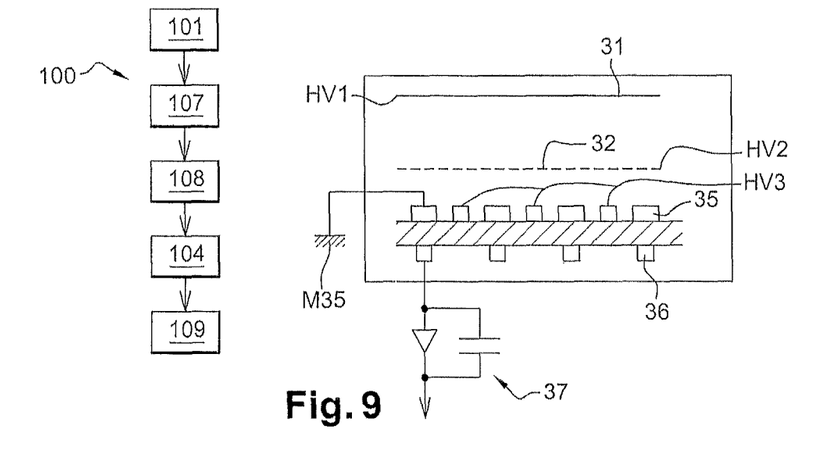
FIG. 9 illustrates a synoptic of the steps of a third mode of implementation of a method for detecting particles in accordance with an embodiment of the invention.

FIG. 9 represents a method 100 for detecting particles operating in amplification optimisation mode and implementing a resistive type particle detection device 30 according to an embodiment of the invention.

In this non-limiting implementation, the method 100 for detecting particles comprises a step 101 of application of a first determined electric voltage HV1 to the cathode 31.

The method 100 further comprises a step 107 of application of a second determined electric voltage HV2 or a voltage ramp (not illustrated) to the amplification micro-gate 32.

It also comprises a step 103 of establishing an electric connection between the reading tracks 36 and the reading system 37.

The method 100 further comprises a step of establishing 104 an electric connection between the resistive tracks 35 and the ground M35.

In addition, the method 100 comprises a step 109 of application of a third determined electric voltage HV3 to the conductive track 38, the third determined electric voltage HV3 being negative. Then, in the same way as with the floating conductive tracks 38, the electric field between the amplification micro-gate 32 and the resistive tracks 35 connected to the ground M35 directs the charges of the electron avalanche linked to the detection to the resistive tracks 35. The fact that the conductive tracks 38 are connected to a negative electric voltage generates an electric field that focuses the collection of charges of the electron avalanche to the resistive tracks 35. For example, the third determined negative electric voltage HV3 is 100V. Moreover, it is desirable that the difference in electric voltage between the amplification micro-gate 32 and the conductive tracks 38, for example 400 V in absolute value, is lower than that between the resistive tracks 35 and the amplification micro-gate 32, for example 500 V in absolute value. In addition, this difference in electric voltage should be sufficiently low so as not to drive sparks between the amplification micro-gate 32 and the conductive tracks 38. The focusing effect induced by an electric voltage on the conductive tracks 38, focusing which pushes back the charges of the electron avalanche, then generates a gain of the resistive type particle detection device 30.

The invention claimed is:

1. A resistive type particle detection device, comprising:
 a cathode;
 an amplification micro-gate;
 an anode composed of a flat insulator comprising resistive tracks arranged on a face of said flat insulator facing the amplification micro-gate and reading tracks arranged on an opposite face of said flat insulator, said reading tracks being connected to a reading system, and
 conductive tracks arranged on said face of said flat insulator facing the amplification micro-gate so as to form an alternation of the resistive tracks and the conductive tracks on an active surface of the particle detection device situated under the amplification micro-gate.

2. The resistive type particle detection device according to claim 1, wherein a number of the conductive tracks is different from a number of the resistive tracks.

3. The resistive type particle detection device according to claim 1, wherein maximum distance separating one of the conductive tracks from a neighbouring resistive track is equal to half of a step separating two resistive tracks situated on either side of the one of the conductive tracks less half of the width of the one of the conductive tracks.

4. The resistive type particle detection device according to claim 1, wherein electric connections of the resistive tracks and/or conductive tracks are situated outside of a sealed enclosure comprising the cathode, the amplification micro-gate, and the anode.

5. The resistive type particle detection device according to claim 1, wherein the resistive tracks and the conductive tracks are physically independent of each other.

6. The resistive type particle detection device according to claim 1, further comprising at least one electric contact, the electric contact being connected at a first end to a first resistive track and at a second end to a second resistive track, one of the conductive tracks positioned between the two resistive tracks being sectioned at a level of the at least one electric contact, two sections of the one of the conductive tracks being connected together via a connection track arranged in the flat insulator.

7. A method for detecting particles implementing a resistive type particle detection device according to claim 1, the method for detecting particles comprising, in particle detection mode:
 applying a first determined electric voltage to the cathode;
 applying a second determined electric voltage to the amplification micro-gate;
 establishing an electric connection between the reading tracks and the reading system;
 establishing an electric connection between the resistive tracks and a ground, and
 establishing a floating connection to the conductive tracks.

8. A method for detecting particles implementing a resistive type particle detection device according to claim 1, the method for detecting particles comprising, in impurities cleaning mode:
 applying a first determined electric voltage to the cathode;
 applying a second determined electric voltage or a voltage ramp to the amplification micro-gate;
 establishing an electric connection between the reading tracks and the reading system or a floating connection of the reading tracks;
 establishing an electric connection between the resistive tracks and a ground, and
 establishing an electric connection between the conductive tracks and a ground.

9. A method for detecting particles implementing a resistive type particle detection device according to claim 1, the method for detecting particles comprising, in amplification optimisation mode:
 applying a first determined electric voltage to the cathode;
 applying a second determined electric voltage or a voltage ramp to the amplification micro-gate;
 establishing an electric connection between the reading tracks and the reading system;
 establishing an electric connection between the resistive tracks and a ground, and applying a third determined electric voltage to the conductive tracks, said third determined electric voltage being negative.

\* \* \* \* \*